United States Patent [19]

Donges et al.

[11] Patent Number: 4,788,704
[45] Date of Patent: Nov. 29, 1988

[54] X-RAY SCANNER & DETECTOR SIGNAL PROCESSING SYSTEM

[75] Inventors: Gerhard Donges, Heidenrod-Kemel; Cornelius Koch, Wiesbaden, both of Fed. Rep. of Germany

[73] Assignee: Heimann GmbH, Fed. Rep. of Germany

[21] Appl. No.: 121,862

[22] Filed: Nov. 17, 1987

Related U.S. Application Data

[63] Continuation of Ser. No. 829,616, Feb. 14, 1986.

[30] Foreign Application Priority Data

Mar. 4, 1985 [DE] Fed. Rep. of Germany ....... 3507607

[51] Int. Cl.$^4$ .................. H05G 1/64; G01N 23/04
[52] U.S. Cl. ................................. 378/99; 378/57; 358/111
[58] Field of Search .............. 378/99, 57, 58, 100; 358/111, 106, 105, 167, 163; 250/359.1, 360.1; 364/574, 517

[56] References Cited

U.S. PATENT DOCUMENTS

| | | | |
|---|---|---|---|
| 3,919,467 | 11/1975 | Peugeot | 378/99 |
| 3,958,078 | 5/1976 | Fowler et al. | 378/57 |
| 4,178,510 | 12/1979 | Wagner | 364/414 |
| 4,366,382 | 12/1982 | Kotowski | |
| 4,383,327 | 5/1983 | Kruger | |
| 4,562,470 | 12/1985 | Dihn et al. | 358/167 |

FOREIGN PATENT DOCUMENTS

| | | | |
|---|---|---|---|
| 0109205 | 5/1984 | European Pat. Off. | 378/19 |
| 0096440 | 4/1985 | European Pat. Off. | |
| 2113828 | 8/1983 | United Kingdom | |

OTHER PUBLICATIONS

"Automated X-Ray Bomb Detection Techniques," Bisognani et al., 8079 Etectro Conf. Record, vol. 4 (1979-04-24/26).
Heimann Brochure Entitled "Komponenten Der Pruftechnik", Aug. 20, 1984.

Primary Examiner—Carolyn E. Fields
Assistant Examiner—Joseph A. Hynds

[57] ABSTRACT

An X-ray device for scanning objects moving on a conveyor path and for processing the detector signals acquired by the scan has a comparator for identifying faulty signals, the comparator being in a control chain for an image storage memory such that, in the event of a faulty detector signal, the contents of a memory row preceding the faulty detector signal are transferred into the memory row into which the faulty detector signal, if a correct signal, would have been stored. The system also includes a correction element for generating a reference signal at 100% radiation intensity in which the mean value of a number of measured signals is formed. The system also includes an element for reducing the amplitude of the useful signal during measurement in comparison to the amplitude allocated to a radiation intensity of 100%.

7 Claims, 1 Drawing Sheet

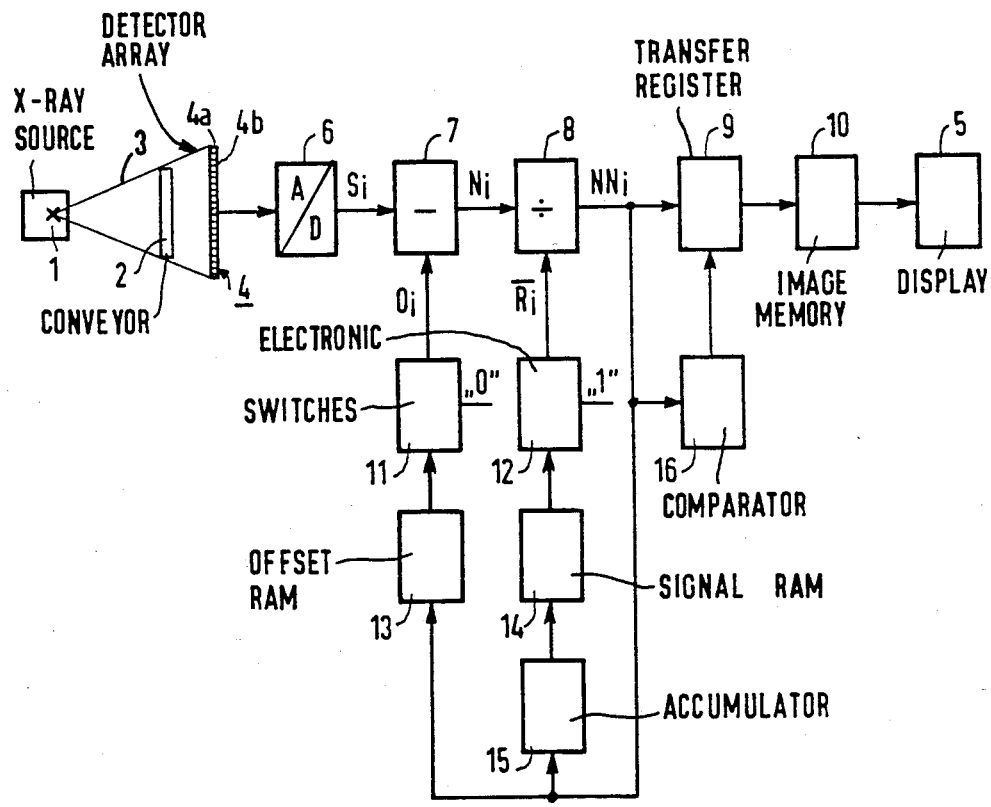

X-RAY SCANNER & DETECTOR SIGNAL PROCESSING SYSTEM

This is a continuation of application Ser. No. 829,616, filed Feb. 14, 1986, now abandoned.

BACKGROUND OF THE INVENTION

1. Field of the Invention

The present invention relates to x-ray scanning devices and signal processing systems, and in particular to an x-ray scanning device for scanning objects moving on a conveyor path and a processor for manipulating the signals acquired by scanning the object.

2. Description of the Prior Art

X-ray scanning devices are known, for example, for examining baggage moving on a conveyor, wherein an x-ray radiator generates a fan-shaped x-ray beam on one side of the object and an array, such as a line, of detectors or sensors disposed on the opposite side of the object receive radiation passing through the object. Such devices also include processing circuitry for acquiring and processing the detector signals and supplying those signals to a display unit. The signal processing circuitry generally includes an image storage memory having a memory row or line for each individual detector.

In such conventional scanning devices, each of the detectors may be a scintillator for converting x-radiation into visible light, which is in turn converted by a photodiode into electrical current. For processing the measured values in parallel, the values are converted by means of electronic switches (analog multiplexers) into a serial sequence of analog measured values. The analog measured values are digitized, systematic errors are compensated, and the resulting value is entered in a digital image storage memory such that a continuous image is generated on a video monitor, which displays the memory contents through a digital-to-analog converter. In a horizontally running picture, data are entered column-by-column into the image memory. Each detector thus generates one line of the video picture.

Various types of systematic errors may occur in such a system. Dark currents of the photodiodes, as well as offset currents of multiplexers and amplifiers, produce an overall offset error which is different for each detector channel. Additonally, amplitude errors may result due to the inequality of the detectors and the emission characteristic of the x-ray source.

Such systematic errors may be compensated in a system having m channels by measuring the offset values ($O_i$) (i=1 . . . m) when the x-ray source is shut off, and storing the offset values in a digital memory (offset RAM). By subtracting the measured offset values from the total signals $S_i$, useful signals $N_i$ are obtained. Amplitude errors result in such a measuring system because the signal amplitudes are measured assuming 100% radiation intensity and, rid of the offset, are stored in the signal memory (signal RAM) as reference values $R_i$. By dividing the signal values $N_i$ by the reference values $R_i$, a useful signal $NN_i$ normalized to 100% is obtained. This is mathematically expressed as follows:

$NN_i = N_i/R_i;$ $i = 1, 2 \ldots m;$ $0 < R_i \leq 1.$

In contrast to the offset measurement, however, acquisition of the different reference values $R_i$ for 100% intensity is also considerably falsified by the quantum noise of the x-ray radiator, particularly given small measured dose values. A further source of error is falsification by electrical noise which may, however, in many instances be negligible. The quantum noise superimposed on the signal is "frozen-in" when the reference values are stored. In the subsequent division, the "frozen-in noise" is amplified by the ratio $1/R_i$. Such "frozen-in noise" generates a streaky image background.

Limits exist for the offset and signal values beyond which processing in an arithmetic unit would result in unacceptable error. If these limits are exceeded, errors are to be anticipated in the visual reproduction. Given a relatively large number of detector channels, for example, 500, outage of individual channels is probable.

SUMMARY OF THE INVENTION

It is an object of the present invention to provide an x-ray scanner and signal processing system wherein the detector signals are processed with significantly reduced error in comparison to conventional devices.

The above object is inventively achieved in a scanning and processing system wherein the processing circuitry includes a comparator for recognizing faulty signals, and wherein the image storage memory is controllable by means including the comparator such that upon the recognition of a faulty detector signal, data from the preceding memory row is transferred into the memory row into which the faulty signal, if it were a correct signal, would have been stored. In the x-ray scanner described herein, the appearance of offset or signal errors of the type described above is detected by the comparator. The appearance of an error prevents transfer of a normalized measured signal value into the image storage memory. In place thereof, the preceding value, which was substantially error-free, is entered. In the visual representation, this means repeating or doubling a line at the location of a faulty channel, however, the effect of such repitition due to this substitution is extremely slight and does not appreciably degrade the video image.

In one embodiment of the invention the processing circuitry includes a correction element for forming a reference signal at 100% radiation intensity by forming the mean value of a plurality of such measured signals. The measuring cycle for the reference signals $R_i$ is executed n times. The measured value of each channel is added n times in an accumulator and is divided by n, according to the mathematical expression:

$$\bar{R}_i = \left( \sum_{j=1}^{n} R_{ij} \right)/n$$

According to well known statistical analysis, the precision of measurement is thereby improved by the factor $\sqrt{n}$.

Considerably more time is available for the measurement of $R_i$ to be repeated at certain time intervals than is available for measurement of the useful signal, for which the duration of the measuring period is limited. The plurality n of measurements can thus be substantially an arbitrary value.

As described above, only measurement of the reference values can be executed a number of times, i.e., can take place over a longer time span than corresponds to a measuring.

The useful signal evaluated for picture formation is thus superimposed with the quantum noise amplitude such as would appear given the acquisition of the reference signal and only one measuring period.

After analog-to-digital conversion, storage and processing of the measured values is undertaken digitally in the system as is known to those skilled in the art. The processible signal amplitude range is defined by the plurality of quantization stages, and the resolution in bits. When the useful signal is normalized to 100% by means of the stored reference values, half of the all of the measured values will lie statistically above 100% signal amplitude, due to the superimposed quantum noise in the useful signal. Signal differences can be acquired up to 100% amplitude, so that information in the form of gray differences in the video picture are lost. Therefore, in accordance with a further embodiment of the invention, means for reducing the amplitude of the useful signal during the measurement in comparison to the amplitude allocated to a radiation intensity of 100% can be provided. Accordingly, the amplitude of the useful signal is reduced by at least half of the maximum amount of the noise voltage to be anticipated after concluding a measuring cycle for the reference signal, so that the signals, including noise, still lie within the acceptable signal range.

DESCRIPTION OF THE DRAWINGS

The single FIGURE is a schematic block diagram of an x-ray scanning and processing system constructed in accordance with the principles of the present invention.

DESCRIPTION OF THE PREFERRED EMBODIMENTS

An x-ray scanner and processing system constructed in accordance with the principles of the present invention is shown in the drawing The system includes an x-ray radiator 1 which generates a fan-shaped x-ray beam 3 encompassing and irradiating material or objects (not shown) on a conveyor 2. The plane of the fan beam 3 is perpendicular to the conveying direction, the conveying direction extending out of the plane of the drawing. The radiation passing through the object and the conveyor 2 is received by a line or row array 4 comprised of a plurality of individual detectors 4a, 4b, etc. The output signals of the individual detectors are supplied through processing circuitry described in greater detail below, to a visual display 5. The processing circuitry includes an analog-to-digital convertor 6, a subtraction unit 7, a divider unit 8, a transfer register 9, and image storage memory 10, two electronic switches 11 and 12, an offset RAM 13, a signal RAM 14, an accumulator 15, and a comparator 16.

The subtraction unit 7, the electronic switch 11 and the offset RAM 13 compensate for the offset values as described above. The offset RAM 13 stores the offset values for all of the channels, with the x-ray source 1 shut off, and the stored offset values are subtracted from the total signal $S_i$ by the subtraction unit 7.

The divider unit 8, the electronic switch 12, the signal RAM 14 and the accumulator 15 operate as described above for generating the reference signal $\overline{R}_i$. In the accumulator 15, the reference values $R_i$ are summed and divided by their plurality n, so that the value $\overline{R}_i$ is at the output of the accumulator 15. This value is stored in the signal RAM 14 and is divided in the divider unit 8 by the respective signal value $N_i$ thereby forming the normalized useful signals $NN_i$.

The comparator 16 detects the appearance of offset or signal errors. An error report in the form of an error bit is separately stored for the offset and the reference signal in the respective RAMs 13 and 14. In the acquisition of the useful signal, the RAMs 13 and 14 are read and the two error bits are logically combined so that the appearance of an error prevents the transfer of a normalized measured signal value into the image memory 10 by an inhibit signal from the comparator 16. The signal from the comparator 16 also causes transfer of the preceding, presumably error-free, value, instead of the faulty value, to the location in the image memory 10 which was reserved for the faulty error signal, if it had been a correct signal.

After concluding the measuring cycle for the reference signal, the amplitude of the useful signal is reduced by the divider 8 as described above.

Although modifications and changes may be suggested by those skilled in the art it is the intention of the inventors to embody within the patent warranted hereon all changes and modificatons as reasonably and properly come within the scope of their contribution to the art.

We claim as our invention:

1. An x-ray device for scanning objects moving on a conveyor path and for processing signals for generating a visual display of said objects comprising:
    means disposed on one side of said conveyor path for directing a fan-shaped x-ray beam at said objects perpendicular to the direction of conveyance of said objects;
    an array of a plurality of x-ray detectors disposed on an opposite side of said conveyor path for detecting radiation passing through said objects;
    an image memory connected to a display means for visually displaying said objects, said image memory having a plurality of memory cells corresponding in number to said plurality of detectors for storing a signal from each detector therein;
    means for controlling entry of signals from said detectors into said memory;
    means for measuring at least one selected type of error in a current detector signal; and
    comparator means connected to said means for measuring for identifying the presence of an unacceptable error in a current detector signal, said comparator means being connected to said means for controlling entry of signals and supplying a signal thereto upon identification of an unacceptable error inhibiting transfer of said current detector signal into said image memory and instead transferring the contents of a selected memory cell preceding the cell allocated for said current detector signal to said cell allocated for said current signal in place of said current signal.

2. An x-ray device as claimed in claim 1, further comprising:
    means for reducing the amplitude of said detector signal during measurement in comparision to an amplitude allocated to a radiation intensity of 100%.

3. An x-ray device as claimed in claim 2, further comprising means for forming a reference signal at 100% radiation intensity.

4. An x-ray device as claimed in claim 3, wherein said means for reducing the amplitude is a divider having an input connected to said detector array, an input connected to said means for generating said reference signal, and an output connected to said means for controlling entry of signals into said image memory.

5. An x-ray device as claimed in claim 4, wherein said means for forming a reference signal is an accumulator having an input connected to said output of said divider.

6. An x-ray device as claimed in claim 5, wherein said accumulator generates a reference signal $\overline{R}_i$ through n cycles according to the formula $$\overline{R}_i = \left( \sum_{j=1}^{n} R_{ij} \right)/n$$

wherein $R_i$ is the measured value of the signal from each of said detectors.

7. An x-ray device for scanning objects moving on a conveyor path, processing signals acquired by said scanning, and displaying said signals on a display means, comprising:

means disposed on one side of said conveyor path for directing a fan-shaped x-ray beam at said objects perpendicular to the direction of conveyance of said objects;

an array of a plurality of x-ray detectors disposed on an opposite of said conveyor path for detecting radiation passing through said objects and for generating a signal corresponding to the detected radiation;

an image memory connected to a display, said image memory having a plurality of memory cells corresponding in number to said plurality of detectors for storing said signal from each detector therein;

means for controlling entry of signals from said detectors into said image memory;

divider means for forming a useful signal of reduced amplitude for each detector signal by dividing each detector signal by a reference signal for a radiation intensity of 100%;

means for generating said reference signal connected to said divider means;

means providing an input to said divider for measuring selected types of errors in said useful signal; and comparator means connected to the output of said divider, said comparator means being connected to said means for controlling entry of signals into said image memory for inhibiting transfer of a current signal upon the identification of an unacceptable error in the output from said divider and instead transferring the contents of a selected memory cell preceding the cell allocated for said current signal to said cell allocated for said current signal in place of said current signal.

* * * * *